United States Patent
Xi et al.

(10) Patent No.: US 8,069,492 B2
(45) Date of Patent: Nov. 29, 2011

(54) SPIN-TORQUE PROBE MICROSCOPE (75) Inventors: Haiwen Xi, Prior Lake, MN (US); Song S. Xue, Edina, MN (US)

(73) Assignee: Seagate Technology LLC, Scotts Valley, CA (US)

( * ) Notice: Subject to any disclaimer, the term of this patent is extended or adjusted under 35 U.S.C. 154(b) by 291 days.

(21) Appl. No.: 12/059,407

(22) Filed: Mar. 31, 2008

(65) Prior Publication Data
US 2009/0242764 A1 Oct. 1, 2009

(51) Int. Cl.
*G01Q 60/08* (2010.01)

(52) U.S. Cl. ............... 850/25; 850/21; 850/26; 850/27; 850/28; 850/29

(58) Field of Classification Search ........ 250/306–443.1
See application file for complete search history.

(56) References Cited

U.S. PATENT DOCUMENTS

| | | | | |
|---|---|---|---|---|
| 5,144,128 A | * | 9/1992 | Hasegawa et al. | 850/9 |
| 5,289,004 A | * | 2/1994 | Okada et al. | 850/1 |
| 5,331,589 A | * | 7/1994 | Gambino et al. | 369/126 |
| 5,375,087 A | * | 12/1994 | Moreland et al. | 850/10 |
| 5,418,363 A | * | 5/1995 | Elings et al. | 850/1 |
| 5,436,448 A | * | 7/1995 | Hosaka et al. | 850/1 |
| 5,670,712 A | * | 9/1997 | Cleveland et al. | 73/105 |
| 5,695,864 A | * | 12/1997 | Slonczewski | 428/212 |
| 5,801,472 A | * | 9/1998 | Wada et al. | 310/309 |
| 5,900,728 A | * | 5/1999 | Moser et al. | 324/244 |
| 5,900,729 A | * | 5/1999 | Moser et al. | 324/244 |
| 5,925,818 A | * | 7/1999 | Cleveland et al. | 73/105 |
| 5,936,237 A | * | 8/1999 | van der Weide | 250/234 |
| 5,994,698 A | * | 11/1999 | Kawade et al. | 850/26 |
| 6,078,174 A | * | 6/2000 | Mukasa et al. | 324/244 |
| 6,094,971 A | * | 8/2000 | Edwards et al. | 73/105 |
| 6,504,152 B2 | * | 1/2003 | Hantschel et al. | 850/56 |
| 6,655,196 B2 | * | 12/2003 | Mukasa et al. | 73/105 |
| 6,714,444 B2 | | 3/2004 | Huai | |
| 7,214,303 B2 | | 5/2007 | Naughton | |
| 7,305,869 B1 | | 12/2007 | Berman | |
| 7,427,754 B2 | * | 9/2008 | Wang et al. | 250/306 |

(Continued)

FOREIGN PATENT DOCUMENTS
EP 348239 A1 * 12/1989

OTHER PUBLICATIONS

K. Wago, D. Botkin, C. S. Yannoni, and D. Rugar, Phys. Rev. B 57, 1108 (1998).
H.J. Mamin, R. Budakian, B.W. Chui, and d. Rugar, Phys. Rev. Lett. 91, 207604 (2003).

(Continued)

*Primary Examiner* — Robert Kim
*Assistant Examiner* — Andrew Smyth
(74) *Attorney, Agent, or Firm* — Mueting, Raasch & Gebhardt PA (57) ABSTRACT

A spin-torque probe microscope and methods of using the same are described. The spin-torque probe microscope includes a cantilever probe body, a magnetic tip disposed at a distal end of the cantilever probe body, an electrically conductive sample disposed proximate to the magnetic tip, an electrical circuit providing a spin-polarized electron current to the electrically conductive sample, and a vibration detection element configured to sense vibration frequency of the cantilever probe body. The spin-polarized electron current is sufficient to alter a local electron spin or magnetic moment within the electrically conductive sample and be sensed by the magnetic tip.

18 Claims, 4 Drawing Sheets

U.S. PATENT DOCUMENTS

| | | | | |
|---|---|---|---|---|
| 7,495,215 | B2 * | 2/2009 | Akinaga et al. | 250/306 |
| 2003/0010099 | A1 * | 1/2003 | Mukasa et al. | 73/105 |
| 2004/0113621 | A1 | 6/2004 | Naughton | |
| 2005/0017171 | A1 * | 1/2005 | Samuelson et al. | 250/306 |
| 2005/0081609 | A1 * | 4/2005 | Worledge | 73/105 |
| 2005/0231225 | A1 * | 10/2005 | Park et al. | 324/762 |
| 2005/0241375 | A1 * | 11/2005 | Naughton | 73/105 |
| 2006/0231754 | A1 * | 10/2006 | Wang et al. | 250/309 |
| 2007/0033993 | A1 * | 2/2007 | Fouchier | 73/105 |
| 2007/0216412 | A1 | 9/2007 | Tsuji | |
| 2007/0235340 | A1 * | 10/2007 | Naughton | 204/667 |

OTHER PUBLICATIONS

D. Rugar, R. Budakian, H.J. Mamin, and B.W. Chui, Nature 430, 329 (2004).

P. Hamel, D. Pelekhov, P. Wigen, T. Gosnell, M. Midzor and M. Roukes, Proc. of the IEEE, vol. 91, vol. 5, pp. 789-798 (2003).

L. Berger, Phys. Rev. B 54, 9353 (1996).

J. Slonczewski, J. Magn. Magn. Mater, 159, L1 (1996): 195, L261 (1999).

S. I. Kiselev, J. C. Snakey, I.N. Krivorotov, N.C. Emley, R.J. Schoelkopf, R.A. Buhrman, D.C. Ralph, Nature 425, 380 (2003).

* cited by examiner

SPIN-TORQUE PROBE MICROSCOPE

BACKGROUND

Since the advent of scanning tunneling microscopy there are a number of techniques such as atomic force microscopy, magnetic force microscopy, and scanning piezo-response microscopy that have emerged for sensitive surface characterization of samples. Magnetic resonance force microscopy is a scanned probe instrument which combines the three-dimensional imaging capabilities of magnetic-resonance imaging with the high sensitivity and resolution of atomic-force microscopy. Magnetic resonance force microscopy enables nondestructive, chemical-specific, high resolution microscopic studies and imaging of subsurface properties of a range of materials.

Magnetic resonance force microscopy incorporates the principles of scanning tunneling microscopy and magnetic resonance-type detections such as electron spin resonance and nuclear magnetic resonance. Magnetic resonance force microscopy is used to detect unpaired electron spins in semiconductor samples known as E' centers and magnetic moments in magnetic samples.

The basic elements of magnetic resonance force microscopy include a mass-loaded cantilever with an attached magnetic tip to sense the force from electron spins or magnetic moments of the sample. An alternating current oscillating microwave magnetic field, in combination with the magnetic field from the magnetic tip, sets up a "resonance slice" in the sample, where the condition of the electron spin resonance is satisfied. The slice is a bowl-shaped surface that extends roughly 250 nm below the magnetic tip and into the sample.

The cantilever with the magnetic tip vibrates in the plane parallel to the sample surface. The frequency of the vibration is picked up by a laser beam shined on the cantilever and through an interferometer. The vibration of the cantilever tip causes the resonant slice to swing back and forth in the sample. When the resonant slice swings through the location of an electron spin, the spin will be cyclically inverted, resulting in a small cantilever frequency shift.

Current magnetic resonance force microscopy utilizes an oscillating microwave magnetic field to excite electron spin resonance. A microwave field of at least 5 Oe oscillating at 3 Ghz is usually required to drive electron spin resonance into the Ghz regime. This set-up is bulky and measurements are usually limited to very low temperatures.

BRIEF SUMMARY

The present disclosure relates to spin-torque probe microscopes and methods of using the same. Spin-torque microscopy utilizes local spin-torque to excite electron spin resonance.

In a first embodiment, a spin-torque probe microscope includes a cantilever probe body, a magnetic tip disposed at a distal end of the cantilever probe body, an electrically conductive sample disposed proximate to the magnetic tip, an electrical circuit providing a spin-polarized electron current to the electrically conductive sample, and a vibration detection element configured to sense vibration frequency of the cantilever probe body. The spin-polarized electron current is sufficient to alter a local electron spin or magnetic moment within the electrically conductive sample and be sensed by the magnetic tip.

In another embodiment, a spin-torque probe microscope includes a cantilever probe body, a magnetic tip disposed at a distal end of the cantilever probe body, an electrically conductive sample disposed proximate to the magnetic tip, an electrical circuit providing a current to the electrically conductive sample, and a vibration detection element configured to sense vibration frequency of the cantilever probe body. The current being sufficient to apply a spin transfer torque to a local electron spin or magnetic moment within the electrically conductive sample and be sensed by the magnetic tip.

In a further embodiment, a method includes placing a magnetic tip of a cantilever probe body proximate to an electrically conductive sample, providing an electrical current through the electrically conductive sample to apply a spin transfer torque to a local electron spin or magnetic moment within the electrically conductive sample, and sensing the spin transfer torque to local the electron spin or magnetic moment within the electrically conductive sample with the magnetic tip.

BRIEF DESCRIPTION OF THE DRAWINGS

The invention may be more completely understood in consideration of the following detailed description of various embodiments of the invention in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to spin-torque probe microscopes and methods of using the same. The spin-torque probe microscope is a microscopic imaging instrument that mechanically detects magnetic resonance signals by measuring the force between a permanent magnet and spin magnetization. Spin-torque microscopy utilizes local spin-torque to excite electron spin resonance. An electrical current is applied on the sample via a point contact. In many embodiments the current is an AC or DC spin-polarized electron current. The current is sufficient to apply a spin transfer torque to local electron spins or magnetic moments within the sample. The spin transfer torque can then be detected by any useful method such as, for example, a cantilever probe body with a magnetic tip. Spin-torque drives the electron spins or magnetic moments into resonance mode and alters, switches, and/or flips the local electron spins or magnetic moments within the sample. The cantilever probe body with a magnetic tip vibrates with the resonance mode and this vibration is altered with the local electron spins or magnetic moments are altered, switches, and/or flips. This vibration and change in vibration can be detected via any useful device such as, for example a cantilever displacement detection element. Spin-torque microscopy results in better spatial resolution of samples than is possible with magnetic resonance force microscopy. While the present invention is not so limited, an appreciation of various aspects of the invention will be gained through a discussion of the examples provided below.

Figure 1:
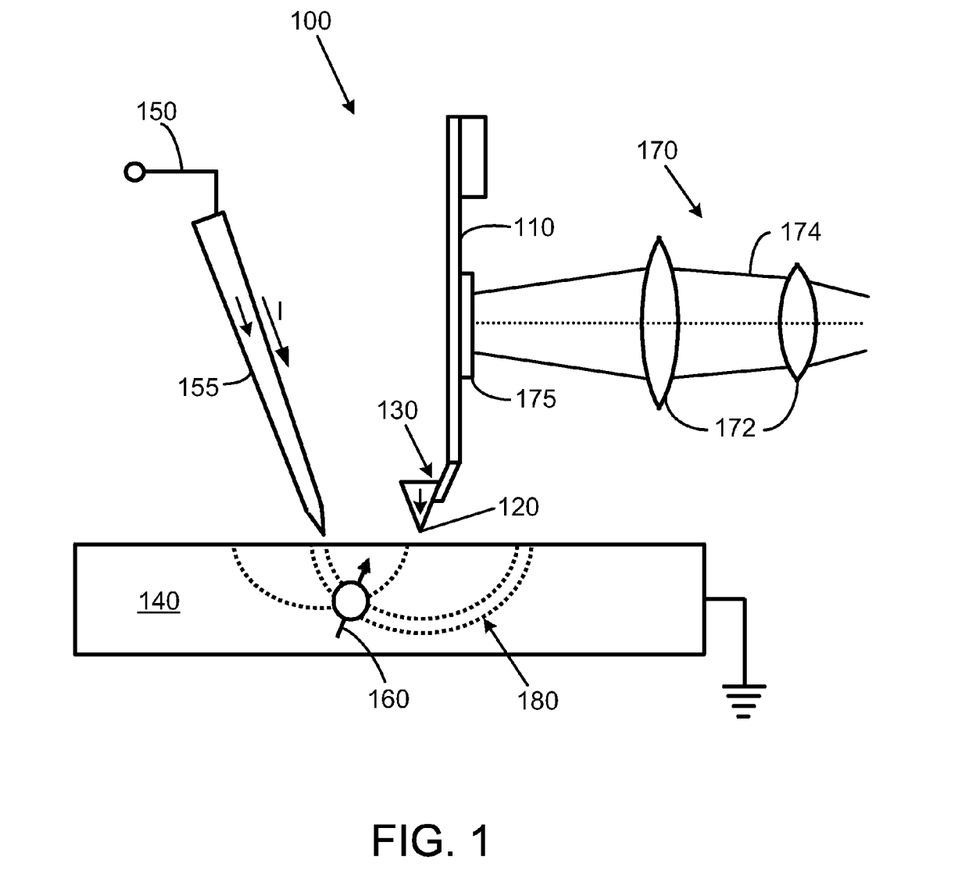
FIG. 1 is a schematic side view of an illustrative spin-torque probe microscope.

FIG. 1 is a schematic side view of an illustrative spin-torque probe microscope 100. The spin-torque probe microscope 100 includes a cantilever probe body 110, a magnetic tip 120 disposed at a terminal or distal end 130 of the cantilever probe body 110, an electrically conductive sample 140 disposed proximate to the magnetic tip 120, an electrical circuit 150 providing electrical current I to the sample 140, and a vibration detection element 170 configured to sense vibration frequency of the cantilever probe body 110.

The electrical circuit 150 provides a current I to the electrically conductive sample 140 sufficient to apply a spin transfer torque to local electron spin or magnetic moment 160 within the electrically conductive sample 140 that is sensed by the magnetic tip 120. In many embodiments the current I is a spin-polarized electron current that is sufficient to alter local electron spin or magnetic moment 160 within the electrically conductive sample 140 and be sensed by the magnetic tip 120. In some embodiments the current I is an alternating current. In some embodiments, the current I is a direct current. In some embodiments the current I is a combination of alternating and direct current. FIG. 1 illustrates the sample electrically conductive sample 140 grounded.

The current I injected locally into the electrically conductive sample 140 in combination with the magnetic field from the magnetic tip 120, sets up a resonance slice 180 in the electrically conductive sample 140, where the condition of the electron spin resonance is satisfied. The resonance slice 140 is a bowl-shaped surface that extends roughly 250 nm below the magnetic tip 120 and into the electrically conductive sample 140. The cantilever probe body 110 with the magnetic tip 120 vibrates in a plane parallel to the electrically conductive sample 140 major surface. The frequency of this vibration is picked up by the vibration detection element 170 (e.g., a laser beam shined on the cantilever and through an interferometer). The vibration of the cantilever probe body 110 magnetic tip 120 causes the resonant slice 180 to swing back and forth in the electrically conductive sample 140. When the resonant slice 180 swings through the location of an electron spin or moment 160, the spin will be cyclically inverted, resulting in a small cantilever frequency shift owing to the magnetic force exerted by the spin or moment 160 on the magnetic tip 120. This cantilever frequency shift is detected or sensed by the vibration detection element 170. In many embodiments, the electron spin resonance is in the gigahertz range, the cantilever vibration frequency is in the kilohertz range, and the detected vibration frequency shift is in the millihertz range.

In FIG. 1 the electrical circuit 150 is electrically connected to an electrically conductive probe 155. The electrically conductive probe 155 provides a point contact where the current I flows to the electrically conductive sample 140. In many embodiments the electrically conductive probe 155 is in physical contact with the electrically conductive sample 140. In other embodiments the electrically conductive probe 155 is proximate to, but not in physical contact with the electrically conductive sample 140. The electrically conductive probe 155 is located proximate to the magnetic tip 120. In many embodiments, the electrically conductive probe 155 is located a distance of 250 nanometers or less from the magnetic tip 120.

The vibration detection element 170 is configured to sense vibration frequency of the cantilever probe body 110. The vibration detection element 170 can measure an amount of displacement of the amplitude of the cantilever probe body 110. The amount of displacement can be measured using any useful displacement detection element such as, for example, an optical interferometer. In the illustrated embodiment, the cantilever probe body 110 includes a light reflecting surface 175 to reflect light from the optical interferometer. The illustrated vibration detection element 170 is an optical interferometer that includes a plurality of lenses 172 to direct light rays 174 and detect an amount of displacement of the amplitude of the cantilever probe body 110.

Figure 2:
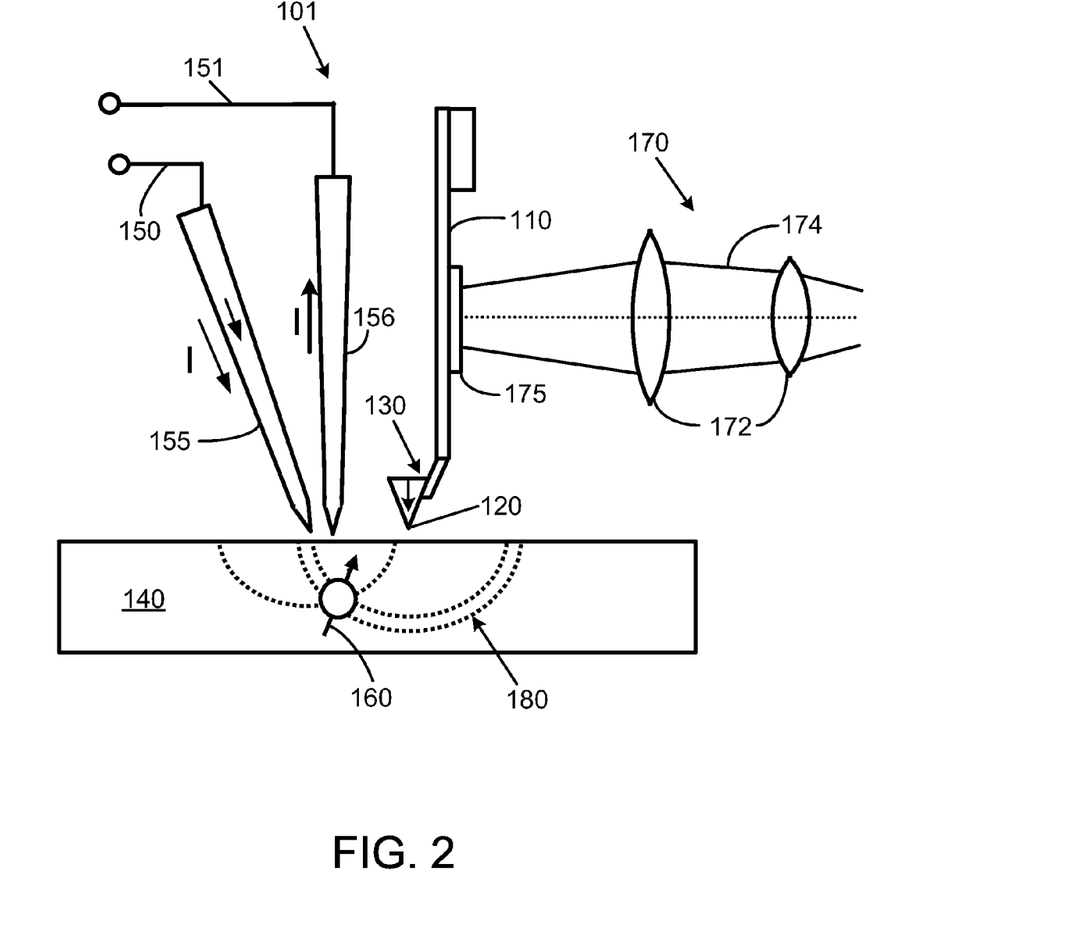
FIG. 2 is a schematic side view of another illustrative spin-torque probe microscope.

FIG. 2 is a schematic side view of another illustrative spin-torque probe microscope 101. The spin-torque probe microscope 101 includes a cantilever probe body 110, a magnetic tip 120 disposed at a terminal or distal end 130 of the cantilever probe body 110, an electrically conductive sample 140 disposed proximate to the magnetic tip 120, an electrical circuit includes an electrical current I source 150 to the sample 140 and an electrical circuit drain 151 from the sample 140, and a vibration detection element 170 configured to sense vibration frequency of the cantilever probe body 110.

The electrical circuit 150, 151 provides a current I to the electrically conductive sample 140 sufficient to apply a spin transfer torque to local electron spin or magnetic moment 160 within the electrically conductive sample 140 that is sensed by the magnetic tip 120. In many embodiments the current I is a spin-polarized electron current that is sufficient to alter local electron spin or magnetic moment 160 within the electrically conductive sample 140 and be sensed by the magnetic tip 120. In some embodiments the current I is an alternating current. In some embodiments, the current I is a direct current. In some embodiments the current I is a combination of alternating and direct current.

The current I injected locally into the electrically conductive sample 140 in combination with the magnetic field from the magnetic tip 120, sets up a resonance slice 180 in the electrically conductive sample 140, where the condition of the electron spin resonance is satisfied. The resonance slice 140 is a bowl-shaped surface that extends roughly 250 nm below the magnetic tip 120 and into the electrically conductive sample 140. The cantilever probe body 110 with the magnetic tip 120 vibrates in a plane parallel to the electrically conductive sample 140 major surface. The frequency of this vibration is picked up by the vibration detection element 170 (e.g., a laser beam shined on the cantilever and through an interferometer). The vibration of the cantilever probe body 110 magnetic tip 120 causes the resonant slice 180 to swing back and forth in the electrically conductive sample 140. When the resonant slice 180 swings through the location of an electron spin or moment 160, the spin will be cyclically inverted, resulting in a small cantilever frequency shift owing to the magnetic force exerted by the spin or moment 160 on the magnetic tip 120. This cantilever frequency shift is detected or sensed by the vibration detection element 170. In many embodiments, the electron spin resonance is in the gigahertz range, the cantilever vibration frequency is in the kilohertz range, and the detected frequency shift is in the millihertz range.

In FIG. 2 the electrical circuit includes an electrical current I source 150 to the sample 140 and an electrical circuit drain 151 from the sample 140. The current I is provided by an electrically conductive probe 155. The electrically conductive probe 155 provides a point contact where the current I flows to the electrically conductive sample 140. The current I is removed from the electrically conductive sample 140 by an electrically conductive probe 156 via a point contact on the electrically conductive sample 140. In many embodiments, one or both of the electrically conductive probes 155, 156 are in physical contact with the electrically conductive sample 140. In other embodiments the one or both of the electrically conductive probes 155, 156 are proximate to, but not in physical contact with the electrically conductive sample 140. The electrically conductive probes 155, 156 are located proximate to the magnetic tip 120. In many embodiments, the one or both of the electrically conductive probes 155, 156 are located a distance of 250 nanometers or less from the magnetic tip 120.

The vibration detection element 170 is configured to sense vibration frequency of the cantilever probe body 110. The vibration detection element 170 can measure an amount of displacement of the amplitude of the cantilever probe body 110. The amount of displacement can be measured using any useful displacement detection element such as, for example, an optical interferometer. In the illustrated embodiment, the cantilever probe body 110 includes a light reflecting surface 175 to reflect light from the optical interferometer. The illustrated vibration detection element 170 is an optical interferometer that includes a plurality of lenses 172 to direct light rays 174 and detect an amount of displacement of the amplitude of the cantilever probe body 110.

The probes 155 and 156 described in FIG. 1 and FIG. 2 can be formed of any useful electrically conductive material. In many embodiments the probe 155 includes a ferromagnetic material that can spin polarize the electrical current I as the electrical current passes through the probe 155.

Figure 3:
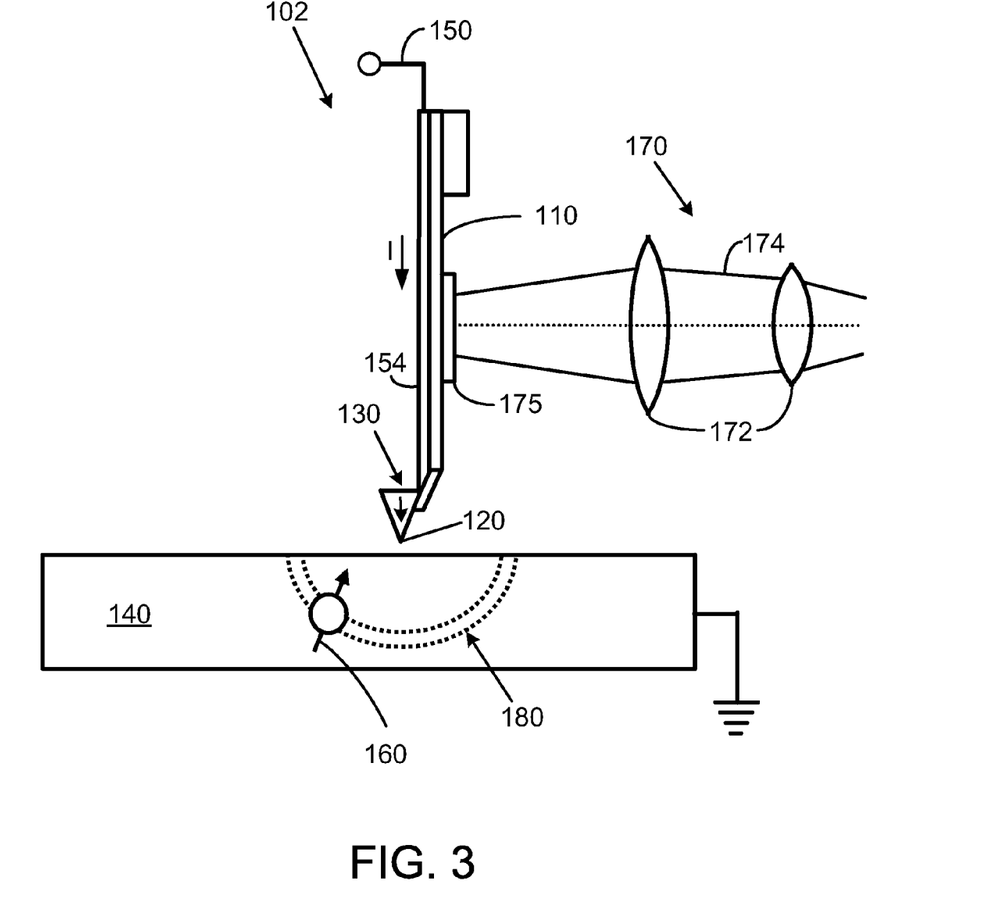
FIG. 3 is a schematic side view of a further illustrative spin-torque probe microscope.

FIG. 3 is a schematic side view of a further illustrative spin-torque probe microscope 102. The spin-torque probe microscope 102 includes a cantilever probe body 110, a magnetic tip 120 disposed at a terminal or distal end 130 of the cantilever probe body 110, an electrically conductive sample 140 disposed proximate to the magnetic tip 120, an electrical circuit 150 providing electrical current I to the sample 140, and a vibration detection element 170 configured to sense vibration frequency of the cantilever probe body 110.

The electrical circuit 150 provides a current I to the electrically conductive sample 140 sufficient to apply a spin transfer torque to local electron spin or magnetic moment 160 within the electrically conductive sample 140 that is sensed by the magnetic tip 120. In many embodiments the current I is a spin-polarized electron current that is sufficient to alter local electron spin or magnetic moment 160 within the electrically conductive sample 140 and be sensed by the magnetic tip 120. In some embodiments the current I is an alternating current. In some embodiments, the current I is a direct current. In some embodiments the current I is a combination of alternating and direct current. FIG. 3 illustrates the sample electrically conductive sample 140 grounded.

The current I injected locally into the electrically conductive sample 140 in combination with the magnetic field from the magnetic tip 120, sets up a resonance slice 180 in the electrically conductive sample 140, where the condition of the electron spin resonance is satisfied. The resonance slice 140 is a bowl-shaped surface that extends roughly 250 nm below the magnetic tip 120 and into the electrically conductive sample 140. The cantilever probe body 110 with the magnetic tip 120 vibrates in a plane parallel to the electrically conductive sample 140 major surface. The frequency of this vibration is picked up by the vibration detection element 170 (e.g., a laser beam shined on the cantilever and through an interferometer). The vibration of the cantilever probe body 110 magnetic tip 120 causes the resonant slice 180 to swing back and forth in the electrically conductive sample 140. When the resonant slice 180 swings through the location of an electron spin or moment 160, the spin will be cyclically inverted, resulting in a small cantilever frequency shift owing to the magnetic force exerted by the spin or moment 160 on the magnetic tip 120. This cantilever frequency shift is detected or sensed by the vibration detection element 170. In many embodiments, the electron spin resonance is in the gigahertz range, the cantilever vibration frequency is in the kilohertz range, and the detected frequency shift is in the millihertz range.

In FIG. 3 the electrical circuit 150 is electrically connected to the cantilever probe body 110 and is electrically connected to the magnetic tip 120 via an electrically conductive path 154. The magnetic tip 120 provides a point contact where the current I flows to the electrically conductive sample 140. The magnetic tip 120 is proximate to, but spaced apart from (i.e., not in physical contact with) the electrically conductive sample 140. The vibration detection element 170 is configured to sense vibration frequency of the cantilever probe body 110. The vibration detection element 170 can measure an amount of displacement of the amplitude of the cantilever probe body 110. The amount of displacement can be measured using any useful displacement detection element such as, for example, an optical interferometer. In the illustrated embodiment, the cantilever probe body 110 includes a light reflecting surface 175 to reflect light from the optical interferometer. The illustrated vibration detection element 170 is an optical interferometer that includes a plurality of lenses 172 to direct light rays 174 and detect an amount of displacement of the amplitude of the cantilever probe body 110.

Figure 4:
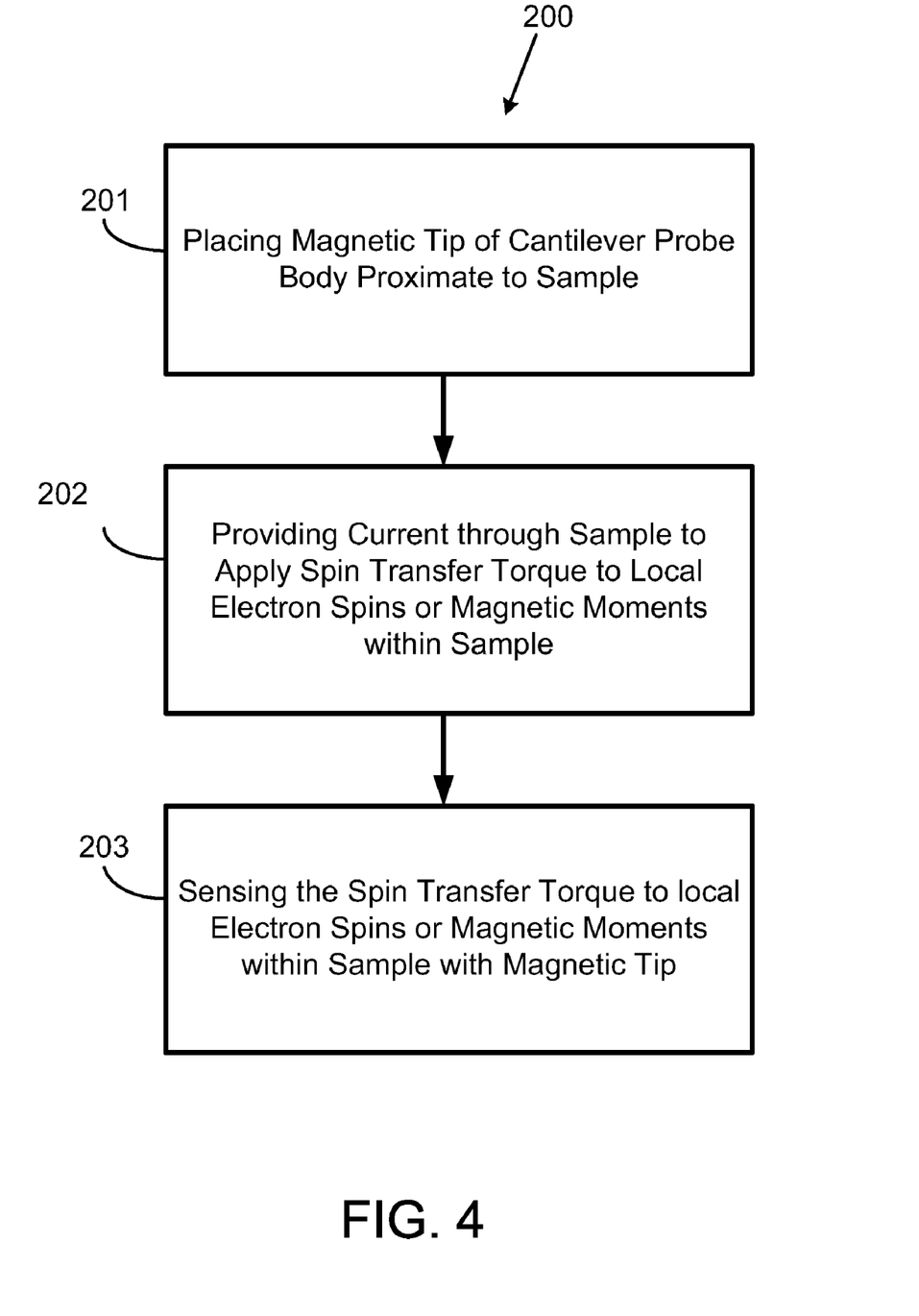
FIG. 4 is a flow diagram of an illustrative method utilizing a spin-torque probe microscope.

FIG. 4 is a flow diagram of an illustrative method 200 utilizing a spin-torque probe microscope. The method 200 includes a step 201 of placing a magnetic tip of the cantilever probe body proximate to the electrically conductive sample. A step 202 includes providing current through the electrically conductive sample which applies a spin transfer torque to local electron spins or magnetic moments within the electrically conductive sample. Then step 203 includes providing the spin transfer torque to local electron spins or magnetic moments within the electrically conductive sample. Relative positions of the magnetic tip and the electrically conductive sample can be changed or scanned to yield a spatial map of the force experienced by the magnetic tip (and attached cantilever body), which translates as a spatial map of the underlying magnetic spin structure of the electrically conductive sample.

Utilizing the spin polarized current with the probe microscope as described herein has a number of advantages over magnetic alternating current fields. These advantages include, for example: (1) the higher the spin polarized current, the larger the spin-torque. It is expected that through the point contact, the spin torque strength can be much larger than the field generated by a microwave coil. Furthermore, the spin polarized current through the point contact will fan out in the sample, resulting a narrow electron spin resonance region that will improve the spatial resolution of the detection since the spin torque gradient will be superposed on the magnetic field gradient of the cantilever tip. Current density for the disclosed probe microscope is about $10^6$ A/cm$^2$, with an applied voltage of less than 5V and a current in a milliamp range. (2) With circuit impedance matching, relatively large alternating current can be achieved in the disclosed probe microscope setup. The disclosed probe microscope is more flexible than the superconductor resonator utilized in probe microscopes based on magnetic alternating current fields. Measurements can be conducted at a wider temperature range including room temperature. (3) Direct current (i.e., DC) spin-current can drive the electron spins or magnetic moments to precession modes. It is possible to utilize DC current for this electron spin or magnetic moment detection. Then, even the circuit impedance matching is not a problem. (4) As mentioned in 1), large spin torque can be achieved at the neighborhood of the point contact. It will be able to detect electron spin resonance beyond the linear regime.

Thus, embodiments of the SPIN-TORQUE PROBE MICROSCOPE are disclosed. The implementations described above and other implementations are within the scope of the following claims. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A spin-torque probe microscope, comprising:
   a cantilever probe body;
   a magnetic tip disposed at a distal end of the cantilever probe body;
   an electrically conductive sample disposed proximate to the magnetic tip;
   an electrical circuit comprising an electrically conductive probe, the electrically conductive probe comprising a probe tip, the probe tip proximate to the magnetic tip, the probe tip providing a spin-polarized electron current to the electrically conductive sample, the spin-polarized electron current sufficient to alter a local electron spin or magnetic moment within the electrically conductive sample and be sensed by the magnetic tip; and
   a vibration detection element configured to sense vibration frequency of the cantilever probe body;
   wherein the electrical circuit comprises a current source probe disposed proximate to and separate from the magnetic tip.

2. A spin-torque probe microscope according to claim 1, wherein the spin-polarized electron current is sufficient to switch the local electron spin or magnetic moment within the electrically conductive sample and be sensed by the magnetic tip.

3. A spin-torque probe microscope according to claim 1, wherein the spin-polarized electron current is provided by an electrically conductive probe comprising a ferromagnetic material and a probe tip.

4. A spin-torque probe microscope according to claim 1, wherein the probe tip is located within 250 nanometers of the magnetic tip.

5. A spin-torque probe microscope according to claim 1, wherein the probe tip is in physical contact with the electrically conductive sample.

6. A spin-torque probe microscope according to claim 1, further comprising a current drain probe disposed proximate to the current source probe.

7. A spin-torque probe microscope according to claim 1, wherein the spin-polarized electron current is a direct current.

8. A spin-torque probe microscope according to claim 1, wherein the spin-polarized electron current is an alternating current.

9. A spin-torque probe microscope according to claim 1, wherein the vibration detection element comprises an optical interferometer.

10. A spin-torque probe microscope, comprising:
    a cantilever probe body;
    a magnetic tip disposed at a distal end of the cantilever probe body;
    an electrically conductive sample disposed proximate to the magnetic tip;
    an electrical circuit comprising an electrically conductive probe, the electrically conductive probe comprising a probe tip, the probe tip proximate to the magnetic tip, the probe tip providing a current to the electrically conductive sample, the current sufficient to apply a spin transfer torque to a local electron spin or magnetic moment within the electrically conductive sample and be sensed by the magnetic tip; and
    a vibration detection element configured to sense vibration frequency of the cantilever probe body
    wherein the electrical circuit comprises a current source probe disposed proximate to and separate from the magnetic tip.

11. A spin-torque probe microscope according to claim 10, wherein the probe tip provides a current to the electrically conductive sample within 250 nanometers of the magnetic tip.

12. A spin-torque probe microscope according to claim 10, further comprising a current drain probe disposed proximate to the current source probe.

13. A method comprising:
    placing a magnetic tip of a cantilever probe body proximate to an electrically conductive sample;
    placing an electrically conductive current source probe proximate to and separate from the magnetic tip;
    providing an electrical current through the electrically conductive current source probe and through the electrically conductive sample to apply a spin transfer torque to a local electron spin or magnetic moment within the electrically conductive sample;
    and sensing the spin transfer torque to the local electron spin or magnetic moment within the electrically conductive sample with the magnetic tip.

14. A method according to claim 13, wherein the sensing step comprises sensing a vibration frequency change in the cantilever probe body.

15. A method according to claim 13, wherein the providing and sensing steps are repeated to a plurality of locations on the electrically conductive sample.

16. A method according to claim 15, further comprising mapping each location and sensed spin transfer torque to the local electron spins or magnetic moments within the electrically conductive sample.

17. A method according to claim 13, wherein the providing step comprises providing a spin-polarized electron current through the electrically conductive sample to apply a spin transfer torque to the local electron spin or magnetic moment within the electrically conductive sample and switch the local electron spin or magnetic moment within the electrically conductive sample.

18. A method according to claim 13, wherein the providing step comprises providing an electrical current to the electrically conductive sample and within 250 nanometers of the magnetic tip.

* * * * *